United States Patent
Fussnegger et al.

(10) Patent No.: US 11,154,508 B2
(45) Date of Patent: Oct. 26, 2021

(54) DRY-BINDERS FOR TABLETS BASED ON POLYETHYLENE GLYCOL-POLYVINYL ALCOHOL GRAFT POLYMERS, THE PRODUCTION AND USE THEREOF

(71) Applicant: BASF SE, Ludwigshafen (DE)

(72) Inventors: Bernhard Fussnegger, Ludwigshafen (DE); Silke Gebert, Ludwigshafen (DE); Felicitas Guth, Ludwigshafen (DE); Karl Kolter, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 126 days.

(21) Appl. No.: 16/624,332

(22) PCT Filed: Jun. 5, 2018

(86) PCT No.: PCT/EP2018/064730
§ 371 (c)(1),
(2) Date: Dec. 19, 2019

(87) PCT Pub. No.: WO2018/234029
PCT Pub. Date: Dec. 27, 2018

(65) Prior Publication Data
US 2020/0129437 A1    Apr. 30, 2020

(30) Foreign Application Priority Data

Jun. 23, 2017 (EP) .................................... 17177620

(51) Int. Cl.
*A61K 9/20* (2006.01)
*A61K 9/08* (2006.01)

(52) U.S. Cl.
CPC .............. *A61K 9/2031* (2013.01); *A61K 9/08* (2013.01); *A61K 9/2009* (2013.01); *A61K 9/2027* (2013.01); *A61K 9/2095* (2013.01)

(58) Field of Classification Search
None
See application file for complete search history.

(56) References Cited

U.S. PATENT DOCUMENTS 6,579,953 B1    6/2003 Gotsche et al.

FOREIGN PATENT DOCUMENTS

WO    WO-00/18375 A1    4/2000

OTHER PUBLICATIONS

Guns et al., Upscaling of the hot-melt extrusion process: comparison between laboratory scale and pilot scale production of solid dispersions with miconazole and Kollicoat® IR, Eur. J. Pharm. Biopharm., 81(3):674-82 (Aug. 2012).
Janssens et al., The use of a new hydrophilic polymer, Kollicoat® IR, in the formulation of solid dispersions of Itraconazole, Eur. J. Pharm. Sci., 30(3-4):288-94 (Mar. 2007).
International Application No. PCT/EP2018/064730, International Search Report and Written Opinion, dated Aug. 9, 2018.
Scheiffele, et al., "An Advantageous Combination for Taste Masking: Kollicoat®", Excipients & Actives for Pharma, AAPS Annual Meeting and Exposition, Toronto, Canada, 2002, 14 pages.

*Primary Examiner* — Nannette Holloman
(74) *Attorney, Agent, or Firm* — Marshall, Gerstein & Borun LLP

(57) ABSTRACT

A finely divided binder in powder form consisting of a polyethylene glycol-polyvinyl alcohol graft polymer particles, wherein the particles have an average particle size D[4,3] in the range of from 10 to 70 μm.

15 Claims, No Drawings

DRY-BINDERS FOR TABLETS BASED ON POLYETHYLENE GLYCOL-POLYVINYL ALCOHOL GRAFT POLYMERS, THE PRODUCTION AND USE THEREOF

CROSS-REFERENCE TO RELATED APPLICATIONS

This application is the U.S. National Stage application of International Patent Application No. PCT/EP2018/064730, filed Jun. 5, 2018, which claims the benefit of European Patent Application No. 17177620.6, filed Jun. 23, 2017.

The present invention relates to binders in powder form based on polyethylene glycol-polyvinyl alcohol graft polymer, where the polyethylene glycol-polyvinyl alcohol graft polymer binders have an average particle size D[4,3] in the range of from 10 to 70 µm and a packing fraction k in the range of from 0.15 to 0.27. The invention further relates to a process for producing such binder particles and to the use thereof as a dry binder in a direct tableting process for producing tablets with high strength.

Binders are ordinarily employed in the production of compressed dosage forms in order to improve the resistance to crushing and the friability. Two tablet production processes normally exist: wet granulation and direct tableting. Binders can be classified according to these applications into wet binders and dry binders. Application of dry binders takes place, as the name suggests, in dry form, that is no dissolving in a solvent takes place. Direct tableting is naturally the more cost-effective process because the individual components need merely to be mixed, but developments frequently fail because an efficient dry binder is not available. Medicinal substances and also many other substances employed in tablets frequently have poor tableting properties, attributable in particular to the impossibility of generating any bonding between the solid particles of these materials during compression, or the materials being so elastic that the bonding is disrupted again on elastic relaxation. It would naturally be possible in principle to compensate this by a high proportion of binder in the tablet. However, this is not expedient because the mass and the volume of the tablet are increased thereby, and it can then scarcely be swallowed. In addition, high proportions of binder prolong the disintegration time and dissolution of the active ingredient. Many medicinal substances therefore cannot be formulated by direct tableting.

The effect of dry binders is also important in roller compaction because it is necessary in this case too for a strong cohesion between the particles of the tablet ingredients to be generated. If this is not the case, the result of the roller compaction is mechanically unstable and disintegrates on comminution again virtually to the initial particle size, flows poorly and provides inadequate resistance to crushing and friability in the subsequent tableting.

A problem associated with some conventional dry binders is their tendency to form peroxides. Such dry binders are unsuitable for oxidation-sensitive active ingredients.

On the other hand, the formulation of active ingredients which are both sensitive to oxidation and hydrolysis is an unsolved problem. For this type of active ingredients wet-granulation is not a feasible method.

At present, no dry binder for dry direct compression mixtures with adequate binder properties for solving these problems is available.

Polyethylene glycol-polyvinyl alcohol graft polymers and their use as coatings agents or binders for wet granulation are described in WO 00/18375.

The use of a commercially available polyethylene glycol-polyvinyl alcohol graft polymer Kollicoat® IR as a wet binder is described by Karl Kolter, AAPS Annual Meeting and Exposition, Toronto, Canada, 2002.

However, this commercially available product is not suited for use in a dry binder direct compression mixture since the resulting tablets are unsatisfactory with regard to tablet hardness and friability.

The problem was solved by finding a binder in powder form based on a polyethylene glycol-polyvinyl alcohol graft polymer where the binder has a mean particle size D[4,3] in the range of from 10 to 70 µm. Preferably, the powderous binder has a packing fraction k in the range of 0.15 to 0.27.

The mean particle size is the D[4,3] volume weighted mean diameter. This parameter can be measured by light scattering. Preferably, the [D4,3] is 10-60 µm, more preferably 15-60 µm, and particularly preferred 15 to 50 µm.

The packing fraction k is the constant of proportionality resulting from the ratio bulk density/true density. This constant is also known as "fractional solids content" and can also be expressed as a percentage.

With the constant k the percentage bed porosity can be calculated as $(1-k) \times 100$.

The polyethylene glycol-polyvinyl alcohol graft polymer which is used for producing the binders according to the invention has polyvinyl alcohol content in the range of 75% b.w. and polyethylene glycol units content in the range of 25% b.w. a. The polyvinyl side chains are produced by grafting a vinyl acetate monomer on the polyethylene glycol chain (PEG 6000) with subsequent saponification of the polyvinyl acetate chain.

The mean molecular weight (weight average) of the graft polymer lies in the range of from 15.000 to 50.000 g/mol. The molecular weight can be determined by SEC-MALLS (size exclusion chromatography-multiple angle light scattering).

A specifically preferred product is commercially available as Kollicoat® IR, Manufacturer BASF SE, Ludwigshafen, and additionally contains colloidal silica in the range of 0.3% b.w., based on solid polymer content, being added as a flowability agent.

This commercial product has a mean particle size in the range of 120 µm and a bulk density of 310 g/l. The true density is 1.03 g/ml. True density is measured at 23° C. according to DIN EN 1183-3, (gas pycnometer). The solubility in water at standard conditions is more than 300 g/l. The weight average molecular weight is in the range of 20.000 g/mol.

According to a preferred embodiment of the invention the finely divided powders are obtained by spray-drying processes.

Spray-drying processes are suitable for producing the products of the invention, and entail a solution of the graft polymers being finely atomized with the aid of spraying devices and then dried in a stream of hot air. Spraying devices can be nozzles or rotating discs, with nozzles as preferred devices.

Aqueous solutions are preferably processed.

Generally, spray conditions can vary over a wide range depending of the size of the spray drying apparatus. The skilled artisan will know how to adapt specific parameters to a given operational capacity.

It is possible to use pressure nozzles or multifluid nozzles for the atomization. Particularly suitable multifluid nozzles are two-substance nozzles. It is crucial that small droplets are achieved and that the dried particles do not stick together.

The atomization takes place at high pressure for the particular type of spraying device. On atomization through pressure nozzles, nozzle diameters of from 0.1 to 3 mm have proved suitable, preferably 0.3 to 2 mm, particularly preferably 0.5 to 1.5 mm.

Pressures in the range of 1 to 50 MPa have proved to be suitable, preferably 5 to 40 MPa, particularly 10 to 30 MPa.

On atomization through two-substance nozzles, nozzle diameters (liquid side) of from 0.1 to 5 mm have proved suitable, preferably 0.3 to 4 mm, particularly preferably 0.5 to 3 mm. Pressures of the atomizing gas 0.03 to 2 MPa have proved suitable, preferably 0.05 to 15 Pa, particularly preferably 0.1 to 10 MPa. Suitable atomizing gases are the same gases as employed for drying as described below.

The solids concentrations of the solutions to be atomized are between 1 and 35% by weight, preferably between 3 and 25% by weight and particularly preferably in the range of from 5 and 15% by weight, for example 5, 7.5, 10, 12.5 and 15% b.w.

In a preferred embodiment, the spray solution is preheated to temperatures in the range of 50-180° C., preferably 60 to 120° C., particularly preferably 70 to 110° C.

The atomization can take place in any spray tower of conventional design. Drying gases which can be used are air or inert gases such as nitrogen, argon or helium, which can be passed through the drying tower co-currently or counter-currently to the liquid droplets. The drying gas is preferably employed co-currently. The tower inlet temperature of the drying gas is from 100 to 200° C., preferably 110 to 180° C. particularly preferably 120 to 170° C. The tower outlet temperature is from 50 to 120° C., preferably 60 to 110° C., particularly preferably 70 to 100° C. The resulting powder can be removed from the gas stream for example via a cyclone or a filter.

The flow-rate of the polymer solution can range from 300 kg/h to 2500 kg/h. The flow of the drying gas can be 10.000 $m^3$/h to 80.000 $m^3$/h According to a specific embodiment of the spray-drying process, a flowability agent can be injected into the spray tower. Suitable flowability agents are finely divided silica or Mg—Al-silicate, Na-AL-silicate, Mg-silicate, Ca-silicate or starches.

The amounts for such agent can be 0.01 to 1% b.w., preferably 0.05 to 0.5% b.w. based on the polymer content of the resulting powder product.

According to another specific embodiment for the process the particle size of the binders of the invention before processing, it is possible for products sprayed in this way to be sieved to even finer average particle sizes. Suitable sieve sizes are 40 μm, 60 μm or 80 μm.

According to another embodiment of the invention to change the particle morphology of the binders, it is possible for products sprayed in this way to be ground using conventional mills such as, for example, air jet mills, pinned-disk mills. Particle sizes can be further adjusted by additional sieving.

According to yet another embodiment commercially available material can be ground using conventional mills such as, for example, air jet mills, pinned-disk mills. Particle sizes can be further adjusted by additional sieving.

In order to produce the dry compression mixture the products of the invention are ordinarily used by mixing with the other ingredients of the formulation and subsequently compressing to a tablet or a compact. The decisive point in this connection is that the dry binder is uniformly distributed in the mixture. In a particular embodiment, it is also possible after the mixing to add water, steam or an organic solvent, thus partly dissolving the small particles and leading to a high strength of the tablet or the compact.

Customary pharmaceutical auxiliaries may optionally be processed at the same time. These take the form of substances of the class of fillers, softeners, solubilizers, additional binders, silicates and also disintegrants and adsorbents, lubricants, flow agents, dyes, stabilizers such as antioxidants, wetting agents, preservatives, release agents, flavorings or sweeteners, preferably fillers, softeners and solubilizers.

The fillers added can be e.g. inorganic fillers such as oxides of magnesium, aluminum or silicon, titanium carbonate or calcium carbonate, calcium phosphates or magnesium phosphates or organic fillers such as lactose, sucrose, sorbitol or mannitol.

Suitable softeners are, for example, triacetin, triethyl citrate, glycerol monostearate, low molecular weight polyethylene glycols or poloxamers.

Suitable solubilizers are surface-active substances having an HLB value (Hydrophilic Lipophilic Balance) greater than 11, for example hydrogenated castor oil ethoxylated with 40 ethylene oxide units (Kolliphor® RH 40), castor oil ethoxylated with 35 ethylene oxide units (Kolliphor EL), polysorbate 80, poloxamers or sodium lauryl sulfate.

The lubricants used may be stearates of aluminum, calcium, magnesium and tin and also magnesium silicate, silicones and the like.

The flow agents used may be, for example, talc or colloidal silicon dioxide.

Suitable additional binders are, for example, microcrystalline cellulose.

A tablet is normally produced in a tablet press, and a compact is produced in a roll compactor. For further processing, the compact is comminuted again to granules which can be mixed with further additives and can for example be compressed to a tablet. The process of roller compaction is also referred to as dry granulation.

The compression to tablets can take place under compressive forces in the range of from 3 to 50 kN, preferably 5 to 40 kN, particularly preferable 5 to 20 kN.

The tablets obtained with the aid of the binders of the invention show a high hardness. The resulting hardness can range from 10 to 500 N, preferably 30 to 300 N, more preferably 50 to 200 N.

The proportion of the dry binder in the formulation can be 0.5-20% by weight, preferably 1-15% by weight and particularly preferably 5-15% by weight.

The fact that the dry binders of the invention have excellent binding properties makes it possible also for poorly compressible active ingredients and excipients to be compressed, especially when they are also present in high concentration.

Normally, powders consisting of fine particles show relatively lower flowability because However, surprisingly, for binders of the invention flowability and angle of repose prove to be unexpectedly good.

It was also surprising that the binders according to the invention do not build up electrostatic charge something which normally expected with small particle sizes.

Binders are frequently tacky substances which increase the ejection force during tableting, thus possibly causing numerous problems such as, for example, reduced strength of the tablet, capping, large rise in temperature of the compression tools and of the die wall, increased wear of the press etc. Entirely unexpectedly, the binders of the invention show a lubricant effect, since the residual and ejection forces during tabletting are distinctly lower than without use of a binder or with use of a conventional binder.

The combined properties of average particle size and fractional solids content is important for the desired properties of the tablets as crushing strength or friability.

In summary, the binders of the invention lead to tablets with exceptional mechanical properties, they make it possible to compress medicinal substances which are compressible with difficulty or not at all, they make it possible to reduce the total tablet mass or the tablet volume, and they ensure that the tabletting process proceeds without impediment.

The binders of the invention are particularly suitable for producing tablets of the following active pharmaceutical ingredients which are normally difficult to compress:
paracetamol, carbamazepine, acetylsalicylic acid, ascorbic acid, metoprolol tartrate, ibuprofen, pseudoephedrine HCl, diphenhydramine HCl, dimenhydrinate, indometacin, diclofenac sodium, N-acetylcysteine, albendazole, alpha-methyldopa, aluminum hydroxides, magnesium silicate, ampicillin, atenolol HCl, captopril, cimetidine, diltiazem, griseofulvin, levamisole, magaldrate, magnesium carbonate, mebendazole, meprobamate, metamizole, metronidazole, neomycin sulfate, oxytetracycline HCl, nitrofurantoin, nystatin, nicotinic acid, phenytoin, piroxicam, pyrazinamide, ranitidine, tetracycline, amoxicillin, chloroquin diphosphate, ethambutol, gemfibrozil, mefenamic acid, metformin HCl, nalidixic acid, naproxen, probenecid, rifampicin, sulfadiazine, sulfadimidine, sulfadoxine, sulfamethoxazole, sulfathiazole, valproic acid, verapamil, aciclovir, allopurinol, bezafibrate, carbidopa, cefuroxime, cephachlor, ciprofloxacin, fenofibrate, alpha-lipoic acid, pentoxyfylline, piracetam, propafenone HCl, roxithromycin, sotalol, sulpiride, tramadol, tilidine.

The binder according to the invention where the binder is a dry-binder for pharmaceutical tablets is particularly characterized by the following preferred embodiments:

EMBODIMENT 1

A finely divided binder in powder form consisting of a polyethylene glycol-polyvinyl alcohol graft polymer particles, wherein the particles have an average particle size D[4,3] in the range of from 10 to 70 µm and a packing fraction k of 0.15 to 0.27, and.

EMBODIMENT 2

A finely divided binder according to Embodiment 1, wherein the average particle size D[4,3] is 10 to 60 µm.

EMBODIMENT 3

A finely divided binder according to Embodiment 1, wherein the average particle size D[4,3] is 15 to 50 µm.

EMBODIMENT 4

A finely divided binder according to Embodiments 1 to 3, wherein the graft copolymer has a polyvinyl alcohol content in the range of 75% b.w. and a polyethylene glycol units content in the range of 25% b.w.

EMBODIMENT 5

A finely divided binder according to any of the Embodiments 1 to 4, wherein the mean molecular weight (weight average) of the graft polymer lies in the range of from 15.000 to 50.000 g/mol.

EMBODIMENT 6

A finely divided binder according to Embodiments 1 to 5, wherein the polyethylene glycol chain of the graft copolymer is a polyethylene glycol with an average molecular weight Mn 6000.

EMBODIMENT 7

A finely divided binder according to any of Embodiments 1 to 6 containing a flowability agent.

EMBODIMENT 8

A finely divided binder according to any of Embodiments 1 to 7, consisting of a polyethylene glycol-polyvinyl alcohol graft polymer and 0.05 to 0.5% b.w., based on the graft polymer, of a flowability agent.

EMBODIMENT 9

A finely divided binder according to any of Embodiments 7 or 8, wherein the flowability agent is colloidal silica.

EMBODIMENT 10

A finely divided binder according to any of Embodiments 1 to 8, containing a polyethylene glycol-polyvinyl alcohol graft polymer with a true density in the range of 1.03 g/ml+/−0.02 g/ml.

EMBODIMENT 11

A process for producing a binder according to any of Embodiments 1 to 10, which comprises adjusting the particle properties of polyethylene glycol-polyvinyl alcohol graft polymer particles to a volume weighted average particle size D[4,3] in the range of from 10 to 70 µm and a packing fraction k of 0.15 to 0.27 by milling or spray-drying.

EMBODIMENT 12

A process for producing a binder according to any of Embodiments 1 to 11, which comprises the steps of (i) providing an aqueous solution of a polyethylene glycol-polyvinyl alcohol graft polymer with a polymer solids content in the range of from 1 to 20% b.w., based on the aqueous solution, and (ii) atomizing the solution into a spray apparatus and drying of the atomized solution to a powder using a drying gas.

EMBODIMENT 13

A process for producing a spray-dried binder according to Embodiment 12, which comprises the steps of heating the aqueous solution provided in step (i) to 50 to 180° C. prior to atomizing the heated solution.

EMBODIMENT 14

A process according to Embodiments 12 and 13, wherein the aqueous solution provided in step (i) is heated to 60 to 120° C. prior to atomizing the heated solution.

EMBODIMENT 15

A process according to any of Embodiments 12 to 14, wherein the aqueous solution provided in step (i) is heated to 70 to 110° C. prior to atomizing the heated solution.

EMBODIMENT 16

A process according to any of Embodiments 12 to 15, wherein a flowability agent is injected into the spray apparatus.

EMBODIMENT 17

A process according to any of Embodiments 12 to 16, wherein the polymer solids content of the spray solution is in the range of from 3 to 25% b.w.

EMBODIMENT 18

A process according to any of Embodiments 12 to 16, wherein the polymer solids content of the spray solution is in the range of from 5 to 15% b.w.

EMBODIMENT 19

A process according to any of Embodiments 12 to 18, wherein the polymer solids content of the spray solution is in the range of from 5 to 12.5% b.w.

EMBODIMENT 20

A process according to any of Embodiments 12 to 19, wherein the atomization step (ii) is carried out using pressure nozzles.

EMBODIMENT 21

A process according to any of Embodiments 12 to 19, wherein the atomization step (ii) is carried out using two-substance nozzles.

EMBODIMENT 22

A process according to any of Embodiments 12 to 21, wherein the tower inlet temperature of the drying gas is in the range of from 100 to 200° C.

EMBODIMENT 24

A process according to any of Embodiments 12 to 22, wherein the tower outlet temperature of the drying gas is in the range of from 50 to 120° C.

EMBODIMENT 25

A process to any of Embodiments 11 to 24, wherein the particle size is further adjusted by a sieving step.

EMBODIMENT 26

A method of manufacturing solid pharmaceutical dosage forms using a finely divided binder in powder form according to any of Embodiments 1 to 24, as a dry-binder for direct compression mixtures.

EMBODIMENT 27

A method of manufacturing solid pharmaceutical dosage forms according to any of Embodiments 1 to 26 wherein the solid pharmaceutical dosage form is a tablet.

EMBODIMENT 28

A method of manufacturing solid pharmaceutical dosage forms according to any of Embodiments 1 to 26 wherein the solid pharmaceutical dosage form is a roller compact.

EMBODIMENT 29

A method of manufacturing solid pharmaceutical dosage forms according to any of Embodiments 1 to 27, wherein the resulting tablets show a hardness of 50 to 200 N.

EMBODIMENT 30

A method of manufacturing solid pharmaceutical dosage forms using a finely divided dry binder in powder form according to any of Embodiments 1 to 27, as a dry-binder for direct compression mixtures, wherein the proportion of the dry-binder in the direct compression mixture is 5-15% b.w.

EXAMPLES

Commercial Kollicoat® IR was used as a starting material with weight average molecular weight in the range of 20.000 g/mol (determined by SEC-MALLS, mobile phase: 0.08 mol/l TRIS-buffer pH 7 in water (+0.15 mol/L NaCl); stationary phase: TSK Gel; standard: pullulan; Detektor: DRI Agilent 1100)

True density was measured at 23° C., according to EN ISO 1183-3 (gas pyknometer):

Gas Pyknometer: Micromeritics, AccuPyc 1340; volume metering chamber 10 $cm^3$; calibration with steel balls.

Prior to the measurement the samples were dried overnight in a vacuum oven (Fa. Heraeus) at 23° C. and 5 hPa.

Measurement was carried out at 23+/−0.1° C. and 1.35 MPa, using argon as measurement gas. Number of specimens tested: three (mass: 2.9782 g; 3.3450 g; 3.2190 g); Arithmetic mean density: 1.03030 g/ml; standard deviation+/−0.5%

True density of the graft copolymer known as commercial Kollicoat® IR: 1.03 g/ml, true densities of the inventive products: 1.03 g/ml.

Particle sizes: volume averaged particle sizes D[4,3] and the respective median d50 were measured using a Malvern Mastersizer 2000.

Bulk densities were measured according to EN ISO 60 using a normed funnel.

Tablet hardness was measured in accordance with Chapter 2.9.8. of the European Pharmacopeia 9 using a Sotax HT 100 tablet tester, the tablet hardness being determined successively on 20 tablets with a speed of the test jaw of 120 mm/min.

Tablet Disintegration was measured according to Chapter 2.9.1. of the European Pharmacopeia 9, Test Method A.

Spray Apparatus:

Products A-D: Niro/Gea Spray Apparatus, Pressure nozzle, diameter 1.2 mm

Product E. Niro Minor, Two-substance nozzle, diameter 1.0 mm

Commercial Kollicoat IR material was used to prepare aqueous solutions with a polymer content of 5, 7.5, 10 and 12.5% bw. respectively.

TABLE 1

| Sprayed product No. | % b.w. of polymer in spray solution |
|---|---|
| A | 5 |
| B | 7.5 |
| C | 10 |
| D | 12.5 |
| E | 10 |

Products A-D:

The aqueous solutions were heated to 80° C. and atomized via three nozzles with a pressure of 20 MPa. The throughput of the spray solution was in the range of 800 kg/h. The inlet temperature of the drying gas (air) was 115° C., the outlet temperature 60° C.

Product E: The particle characteristics of the resulting powders are listed in Table 2.

Two-substance nozzle diameter 1.0 mm; Inlet air: 120° C.; outlet air 65° C.; feed rate 17 g/min; nozzle pressure: 0.4 MPa

TABLE 2

Powder particle characteristics

| Spray product No. | D [4, 3] [μm] | d50 [μm] | Bulk density [g/l] | Packing fraction k | Angle of Repose [°] |
|---|---|---|---|---|---|
| A | 36 | 33 | 200-220 | 0.194-0.214 | 20-25 |
| B | 49 | 45 | 198-218 | 0.192-0.212 | 20-25 |
| C | 59 | 54 | 214-222 | 0.208-0.216 | 20-25 |
| D | 66 | 60 | 240-254 | 0.233-0.247 | 20-25 |
| E | 10 | 6 | 190-220 | 0.184-0.214 | 20-25 |
| A; sieved | 23 | 22 | 190-210 | 0.184-0.204 | 20-25 |
| Comparative Ex. Kollicoat IR | 120 | 106 | 310 | 0.301 | 20-25 |
| Kollicoat IR, milled | 17 | 15 | nd | nd | nd |

Tableting Experiments

TABLE 3

Direct compression mixtures with inventive binders

| No. DCM | Dicafos [% b.w.] | Kollidon CL_F [% b.w.] | Mg stearate [% b.w.] | Inventive binder [% b.w.] |
|---|---|---|---|---|
| 1 | 94.5 | 2.5 | 0.5 | 2.5 |
| 2 | 92.0 | 2.5 | 0.5 | 5 |
| 3 | 89.5 | 2.5 | 0.5 | 7.5 |
| 4 | 87.0 | 2.5 | 0.5 | 10 |
| 5 | 82.0 | 2.5 | 0.5 | 15 |
| 6 | 77.0 | 2.5 | 0.5 | 20 |

Dicafos A60: direct compressible anhydrous dicalcium phosphate, bulk density 1300-1400 g/l, Chemische Fabrik Budenheim Kollidon® CL-F: Crospovidone, BASF SE, bulk density 0.18-0.28 g/ml; Particle size sieve fraction: more than 95%<250 μm In addition, spray product A was sieved to a median particle size d50 of 22 μm. and used for the tableting experiments described below.

Also, Kollicoat IR powder was milled to the particle size listed in Table 2 and used in a tableting mixture. Milling was carried out using a countercurrent fluidized bed mill AFG 100 (Alpine). Mill settings: 3 nozzles of 1.9 mm diameter; grinding gas pressure of 0.6 Pa; gas throughput 55.0 m$^3$/h; 50 mm diameter deflector wheel; rotational speed 8000 rpm; 21 m/s tip speed; 0.7 kg/h product throughput, trial time 20 min; amount of ground product: 5 kg For Comparison: Direct Compression Mixtures without Inventive Binder:

Comparative Ex. I

Dicafos A60 97.0%
Kollidon Cl—F 2.5%
Mg-stearate 0.5%

Comparative Ex. II

Dicafos A60 87.0%
Kollidon Cl—F 2.5%
Mg-stearate 0.5%
Kollicoat® IR 10%

The direct compression mixtures were pressed to tablet under the following conditions:

The individual components were sieved through a 0.8 mm sieve and then blended in ab turbula mixer (T10B) for 8 min. After addition of magnesium stearate the powders were blended for a further 2 min. The resulting powder blends were compressed into tablets on a single punch press (EK0, Korsch) with a punch diameter of 10 mm (biplanar) applying 5, 7.5, 10, 12.5 and 15 kN, respectively.

The tablets were tested for hardness as described above. The results are listed in Table 4.

TABLE 4

| DCM No./ Spray Product, Particle Size Distr. | Tablet Hardness [N] at different compression forces [kN] | | | | |
|---|---|---|---|---|---|
| | 5 kN | 7.5 kN | 10 kN | 12.5 kN | 15 KN |
| Comp. DCM I/ 0% | n/m | n/m | 9 | 13 | 17 |
| DCM 1, Product A, d50 = 33 μm | 7 | 18 | 24 | 38 | 50 |
| DCM 2, Product A, sieved, d50 = 22 μm | 12 | 28 | 43 | 62 | 76 |
| DCM 2, Product A, d50 = 33 μm | 10 | 23 | 36 | 51 | 65 |
| DCM 3, Product A, sieved, d50 = 22 μm | 16 | 34 | 52 | 73 | 91 |
| DCM 3, Product A, d50 = 33 μm | 14 | 35 | 55 | 79 | 104 |
| DCM 4, Product A sieved, d50 = 22 μm | 22 | 50 | 80 | 107 | 138 |
| DCM 4, Product A, d50 = 33 μm | 15 | 41 | 68 | 82 | 109 |
| DCM 4, Product B, d50 = 45 μm | 14 | 38 | 60 | 90 | 114 |
| DCM 4, Product C, d50 = 54 μm | 22 | 47 | 62 | 71 | 92 |
| DCM 4, Product D, d50 = 60 μm | 17 | 36 | 62 | 97 | 125 |
| DCM, 5 Product | 35 | 72 | 126 | 155 | 183 |

TABLE 4-continued

| DCM No./Spray Product, Particle Size Distr. | Disintegration time [s] obtained at different compression forces [kN] | | | | |
|---|---|---|---|---|---|
| | 5 kN | 7.5 kN | 10 kN | 12.5 kN | 15 KN |
| A, d50 = 33 µm | | | | | |
| DCM 6, Product A, d50 = 33 µm | 63 | — | 143 | — | 213 |
| DCM 4, Product E, d50 = 6 µm | 25 | 40 | 68 | 91 | 122 |
| Comp. Ex. II d50 = 106 µm | n/m | n/m | 8 | 26 | 37 | n/m : not measurable, due to insufficient stability

| DCM No./Spray Product, Particle Size Distr. | Disintegration time [s] obtained at different compression forces [kN] | | | | |
|---|---|---|---|---|---|
| | 5 kN | 7.5 kN | 10 kN | 12.5 kN | 15 KN |
| Comp. DCM I/ 0% | n/m | n/m | 2 | 3 | 2 |
| DCM 1, Product A, d50 = 33 µm | 3 | 2 | 6 | 4 | 5 |
| DCM 2, Product A, sieved, d50 = 22 µm | 9 | 14 | 12 | 10 | 11 |
| DCM 2, Product A, d50 = 33 µm | 6 | 9 | 10 | 11 | 9 |
| DCM 3, Product A, sieved, d50 = 22 µm | 25 | 21 | 21 | 21 | 25 |
| DCM 3, Product A, d50 = 33 µm | 18 | 15 | 11 | 14 | 20 |
| DCM 4, Product A sieved, d50 = 22 µm | 56 | 52 | 83 | 127 | 228 |
| DCM 4, Product A, d50 = 33 µm | 20 | 25 | 21 | 23 | 40 |
| DCM 4, Product B, d50 = 45 µm | 16 | 17 | 14 | 18 | 23 |
| DCM 4, Product C, d50 = 54 µm | 13 | 13 | 16 | 13 | 15 |
| DCM 4, Product D, d50 = 60 µm | 9 | 7 | 12 | 15 | 18 |
| DCM 4, Product E, d50 = 58 µm | 11 | 14 | 15 | 13 | 17 |
| DCM 5, Product A, d50 = 33 µm | 53 | 96 | 258 | 269 | 466 |
| DCM 6, Product A, d50 = 33 µm | 279 | nd | 600 | nd | 749 |
| DCM 4, Product E, d50 = 6 µm | 23 | 29 | 25 | 23 | 31 |
| DCM 4, Kollicoat IR milled, d50 = 15 µm | 27 | 33 | 21 | 22 | 31 |
| Comp. Ex. II/ d50 = 106 µm | nd | nd | 5 | 4 | 5 |

Nd: not determined, tableting not possible

The invention claimed is:

1. A finely divided binder in powder form consisting of a polyethylene glycol-polyvinyl alcohol graft polymer particles, wherein the particles have an average particle size D[4,3] in the range of from 10 to 70 µm.

2. The finely divided binder according to claim 1, wherein the particles have an average particle size D[4,3] in the range of from 10 to 70 µm and a packing fraction k of 0.15 to 0.27, and where the binder is a dry-binder for pharmaceutical tablets.

3. The finely divided binder according to claim 1, wherein the graft copolymer has a polyvinyl alcohol content in the range of 75% b.w. and a polyethylene glycol units content in the range of 25% b.w.

4. The finely divided binder according to claim 1, wherein the average particle size D[4,3] is 10 to 60 µm.

5. The finely divided binder according to claim 1 wherein the average particle size D[4,3] is 15 to 50 µm.

6. The finely divided binder according to claim 1, containing a flowability agent.

7. The finely divided binder according to claim 1, consisting of a polyethylene glycol-polyvinyl alcohol graft polymer and 0.05 to 0.5% b.w., based on the graft polymer, of a flowability agent.

8. The finely divided binder according to claim 6, wherein the flowability agent is colloidal silica.

9. The process for producing a binder according to claim 1, which comprises adjusting the particle properties of polyethylene glycol-polyvinyl alcohol graft polymer particles to a volume weighted average particle size D[4,3] in the range of from 10 to 70 µm by milling or spray-drying.

10. The process for producing a binder according to claim 1, which comprises adjusting the particle properties of polyethylene glycol-polyvinyl alcohol graft polymer particles to a volume weighted average particle size D[4,3] in the range of from 10 to 70 µm and a packing fraction k of 0.15 to 0.27 by milling or spray-drying.

11. The process for producing a binder as claimed in claim 1, which comprises the steps of (i) providing an aqueous solution of a polyethylene glycol-polyvinyl alcohol graft polymer with a polymer solids content in the range of from 1 to 35% b.w., based on the aqueous solution, and (ii) spray drying by atomizing the solution into a spray apparatus.

12. The process for producing a spray-dried binder according to claim 11, which comprises the steps of heating the aqueous solution provided in step (i) to 50 to 180° C. prior to atomizing the heated solution.

13. The process according to claim 12 wherein the aqueous solution provided in step (i) is heated to 60 to 120° C. prior to atomizing the heated solution.

14. The process according to claim 9, wherein a flowability agent is injected into the spray apparatus.

15. The method of manufacturing solid pharmaceutical dosage forms using a finely divided binder in powder form according to claim 1, as a dry-binder for direct compression mixtures.

* * * * *